(12) United States Patent
Hunt et al.

(10) Patent No.: US 7,321,428 B2
(45) Date of Patent: Jan. 22, 2008

(54) PROCESS PHOTOMETER

(75) Inventors: Robert N. Hunt, Steubenville, OH (US); Atul Khettry, Wheeling, WV (US); Matthew R. Vila, Wheeling, WV (US)

(73) Assignee: Bayer MaterialScience LLC, Pittsburgh, PA (US)

( * ) Notice: Subject to any disclaimer, the term of this patent is extended or adjusted under 35 U.S.C. 154(b) by 280 days.

(21) Appl. No.: 11/021,202

(22) Filed: Dec. 22, 2004

(65) Prior Publication Data

US 2006/0132779 A1   Jun. 22, 2006

(51) Int. Cl.
*G01N 21/25* (2006.01)
(52) U.S. Cl. ...................... 356/418; 356/414
(58) Field of Classification Search ............ None
See application file for complete search history.

(56) References Cited

U.S. PATENT DOCUMENTS

| | | | | |
|---|---|---|---|---|
| 3,762,817 A * | 10/1973 | Harklau | ................. | 356/73 |
| 4,233,512 A * | 11/1980 | Rupert | ................. | 250/338.1 |
| 4,274,744 A * | 6/1981 | Chae et al. | ................. | 356/414 |
| 4,785,806 A * | 11/1988 | Deckelbaum | ................. | 606/7 |
| 4,832,490 A * | 5/1989 | Boos et al. | ................. | 356/325 |
| 4,968,148 A * | 11/1990 | Chow et al. | ................. | 356/427 |
| 5,151,474 A | 9/1992 | Lange et al. | ................. | 526/60 |
| 5,170,056 A | 12/1992 | Berard et al. | ................. | 250/341 |
| 5,287,423 A | 2/1994 | Anthony | ................. | 385/26 |
| 5,763,883 A | 6/1998 | Descales et al. | ...... | 250/339.09 |
| 5,825,478 A | 10/1998 | Wilcox et al. | ................. | 356/73 |
| 6,300,633 B1 | 10/2001 | Hunt et al. | ............. | 250/339.12 |
| 6,429,936 B1 * | 8/2002 | Scaduto | ................. | 356/417 |
| 6,730,909 B2 * | 5/2004 | Butler | ................. | 250/338.1 |
| 2002/0121043 A1 * | 9/2002 | Hawkins | ................. | 43/42.09 |

* cited by examiner

*Primary Examiner*—Layla G. Lauchman
*Assistant Examiner*—Jonathan Skovholt
(74) *Attorney, Agent, or Firm*—Noland J. Cheung; Lyndanne M. Whalen

(57) ABSTRACT

A process photometer which includes an insulated and a non-insulated compartment. The insulated compartment is maintained at a relatively constant, elevated temperature. The radiation source, a rotatable filter wheel, a radiation detector, and a means for converting analog output to a digital signal are among the components within the insulated compartment. The non-insulated compartment houses a power supply.

25 Claims, 9 Drawing Sheets

Photometer Back View

Photometer Isometric NE View

Photometer Isometric NW View

Photometer Isometric SE View

Photometer Isometric SW View

Photometer Left View

Photometer Right View

Photometer Front View

Photometer Back View

Filter Wheel Assembly Cut Away View

PROCESS PHOTOMETER

BACKGROUND OF THE INVENTION

The present invention relates to a process photometer for monitoring a production process in which such photometer is used.

In-line monitoring of chemical processes makes it possible to reduce production cycle time, improve the safety of such processes and reduce waste. A number of methods for such monitoring with conventional analytical devices have been disclosed in the literature. Two general approaches have been taken in developing such monitoring processes. In one approach, the amount of energy absorbed by a sample or selected material is measured and compared to one or more pre-established standards. Examples of this approach may be found in U.S. Pat. Nos. 5,151,474; 5,170,056; and 5,763,883.

U.S. Pat. No. 5,151,474, for example, discloses a polyolefin polymerization process in which the rate of addition of the principal monomer is controlled on the basis of a vibrational spectroscopy analysis (e.g., Fourier Transform infrared spectroscopy) of that monomer's concentration in the reactor. In this method, the chemical analysis may be conducted either on-line or off-line. On-line analysis is conducted by directing a portion of the process stream directly to the process analyzer. Such diversion is not, however, desirable in many production environments.

U.S. Pat. No. 5,170,056, discloses an infrared probe for in situ sensing of infrared energy absorption in a sample. This probe which senses the amount of infrared energy absorbed in a sample is designed to make it possible to determine infrared spectroscopic signatures at a point remote from a standard spectrometer.

U.S. Pat. No. 5,763,883 discloses a method for determining or predicting a value of a selected property of a material being produced in which the absorption of the selected material is measured at more than one wavelength and the measured wavelengths are compared to standards.

Another approach taken in monitoring commercial chemical production processes is the photometric approach in which the radiation absorbed by a sample at predefined wavelengths and bandwidths is evaluated in relation to a pre-established standard. Examples of this photometric approach are found in U.S. Pat. Nos. 4,968,148 and 5,825,478.

U.S. Pat. No. 4,968,148 discloses a single source multisite photometric system in which a number of isolated samples on a sample plate may be analyzed for kinetic and/or end-point densitometric properties in rapid sequence. This system is not, however, capable of monitoring a production process as that process is being conducted. The samples must be collected and analyzed at a remote location.

U.S. Pat. No. 5,825,478 discloses a multifunctional photometer in which electromagnetic radiation from a source which has been sent through a sample cell is analyzed substantially instantaneously by multiple detectors at multiple wavelengths from a broad band electromagnetic radiation source. The use of multiple detectors, however, increases the costs associated with the construction and maintenance of the photometer. In addition, the use of beam splitters to direct a portion of the electromagnetic radiation to each detector reduces the total signal that would be available if only one detector were used. In many cases, the energy available at the detector has been attenuated to marginal levels either by the constituent of interest, or scattering from suspended particles.

An accurate photometric device having a minimum number of components which is durable, inherently stable, and compact, may be housed in an explosion proof enclosure, that does not require instrument air or nitrogen purging for explosion proof rating or cooling, and which has been optimized for maximum optical throughput and signal to noise ratio, so that it can be permanently installed at a location close to the stream of material to be monitored would be advantageous.

SUMMARY OF THE INVENTION

It is an object of the present invention to provide a photometer with a minimum number of moving components subject to excessive mechanical wear.

It is another object of the present invention to provide a photometer that maximizes total optical throughput for optimum signal to noise ratio, and minimizes alignment criteria for stable, low maintenance operation.

It is also an object of the present invention to optimize component layout to reduce stress and strain on optical components that would affect alignment and stability.

It is a further object of the present invention to provide a photometer in which thermally dependent components are positioned in a temperature-controlled compartment.

It is another object of the present invention to provide a photometer that can be easily installed in a chemical production unit next to the sample point of interest by packaging the photometer in a small housing that provides an explosion proof rating for operation in areas with Class I Division 1 Groups B,C,D classification without additional gas purging or electrical interlocks.

It is an additional object of the present invention to provide a photometer with enough wavelength specific band-pass filters that it is possible to monitor a chemical production process in-line where a spectrometer scanning a continuum of wavelengths and employing chemometrics was previously required.

These and other objects which will be apparent to those skilled in the art are accomplished by the photometer and the method for photometric process analysis of the present invention described more fully herein.

DETAILED DESCRIPTION OF THE PRESENT INVENTION

Figure 1:
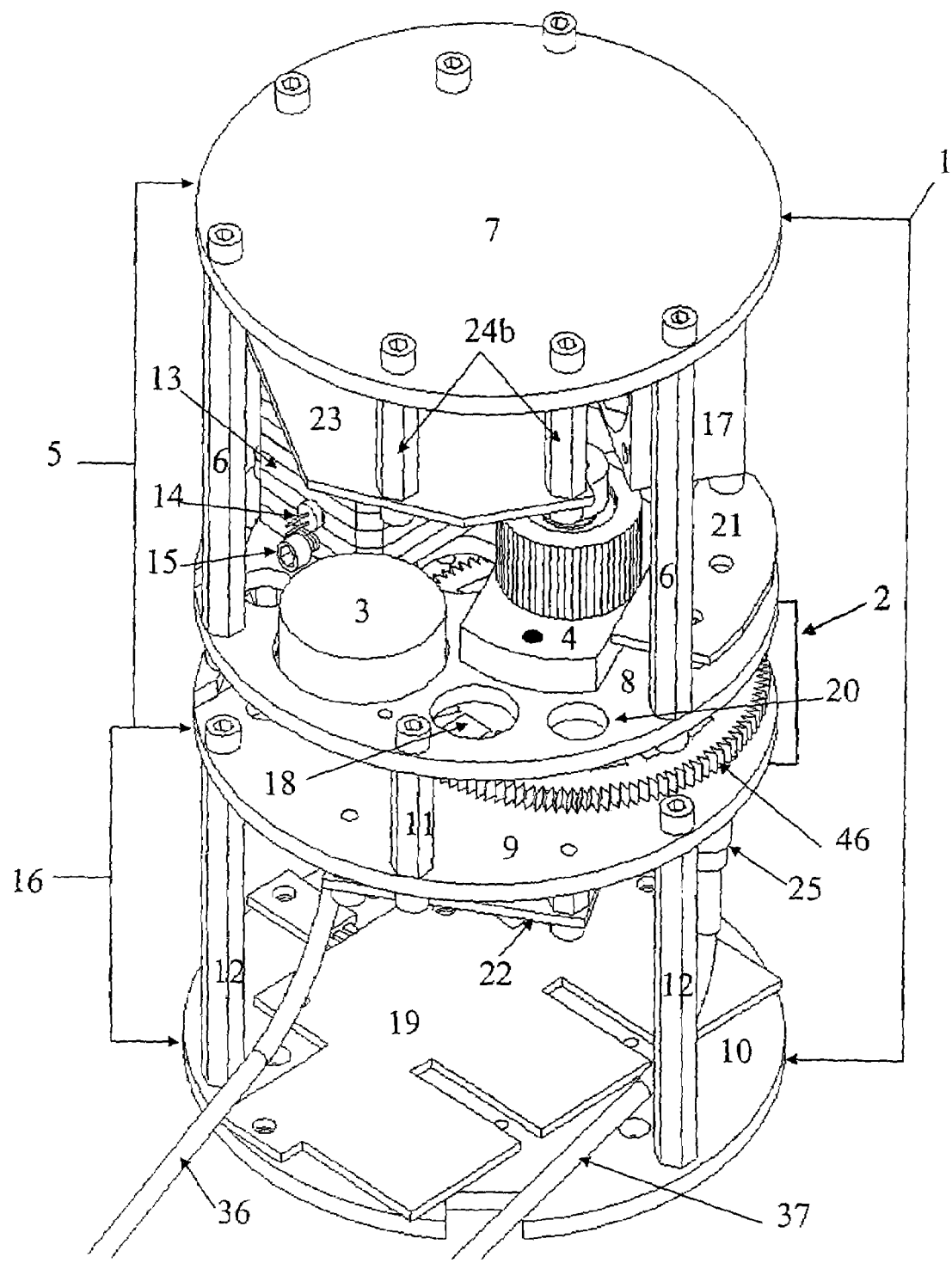
FIG. 1 is a component placement representation of the northeastern isometric view of the photometer of the present invention.
Figure 2:
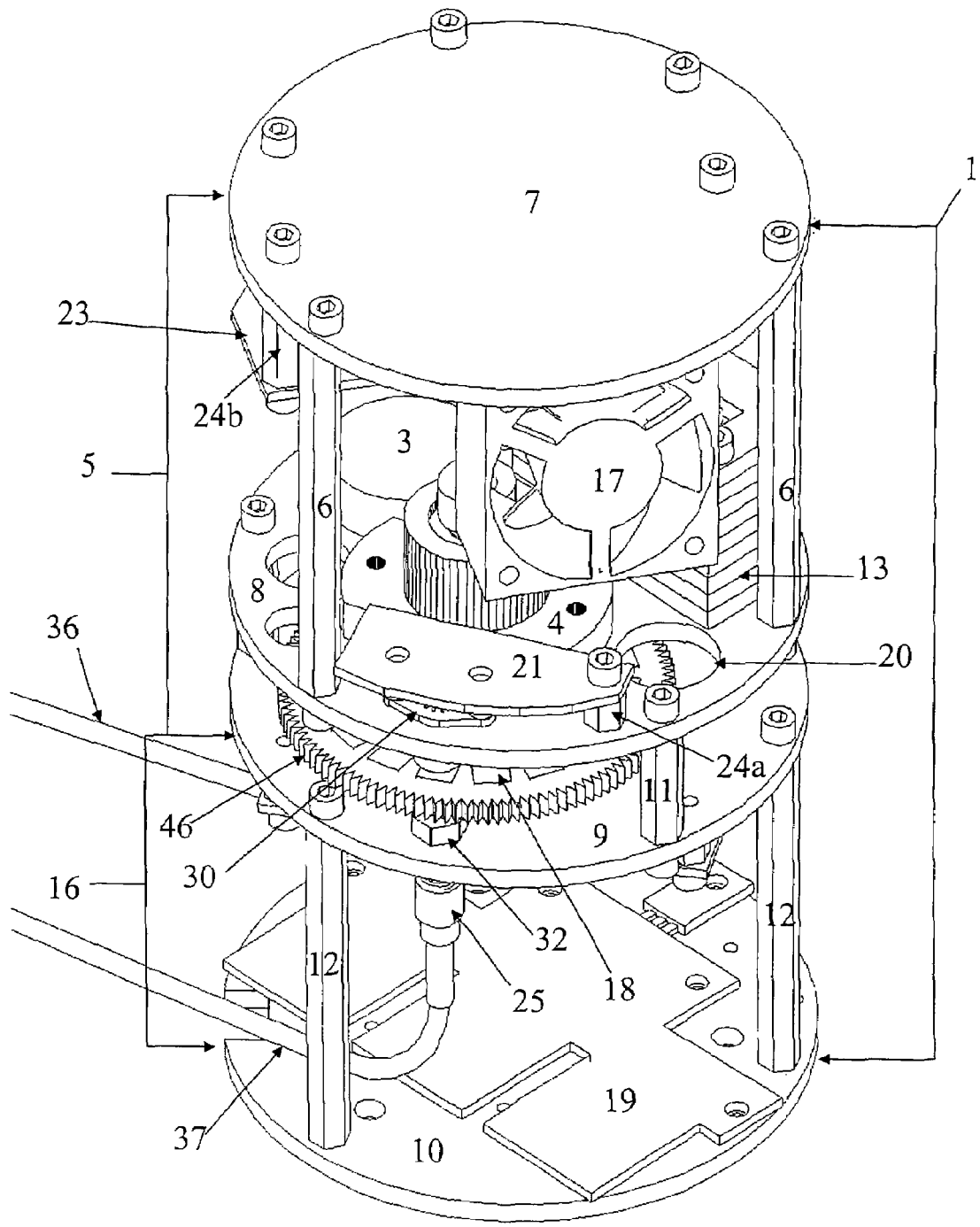
FIG. 2 is a component placement representation of the northwestern isometric view of the photometer of the present invention.
Figure 3:
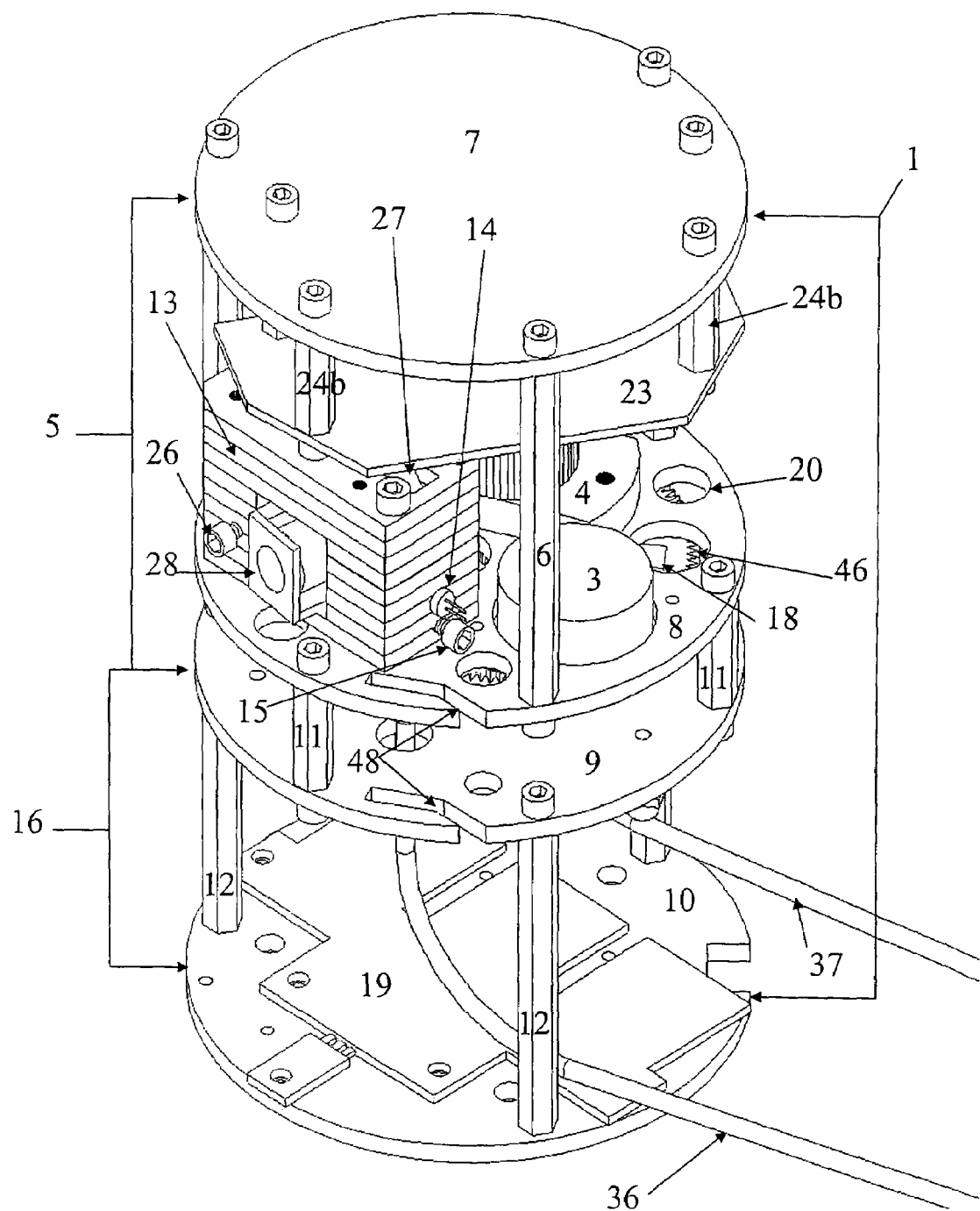
FIG. 3 is a component placement representation of the southeastern isometric view of the photometer of the present invention.
Figure 4:
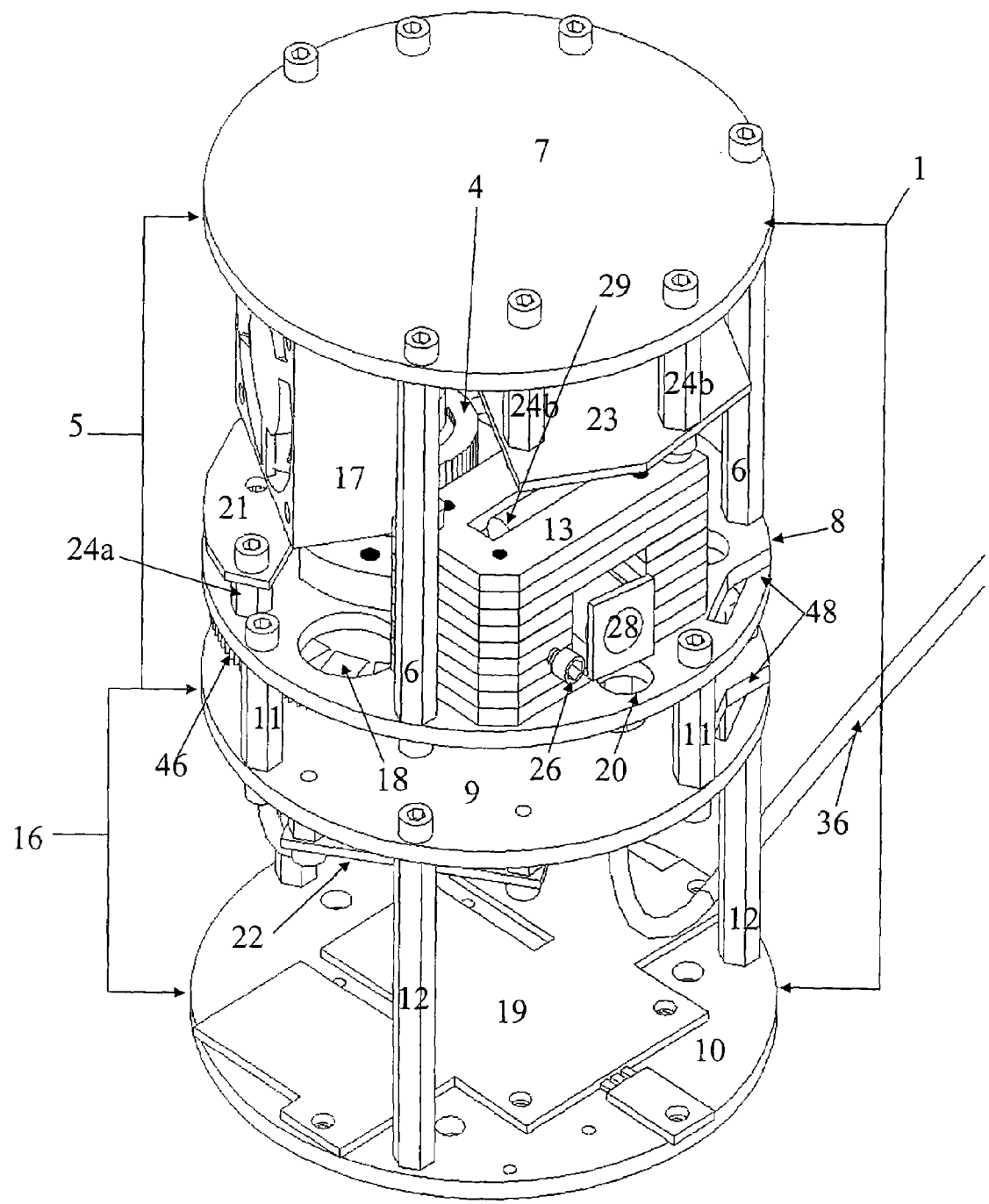
FIG. 4 is a component placement representation of the southwestern isometric view of the photometer of the present invention.
Figure 5:
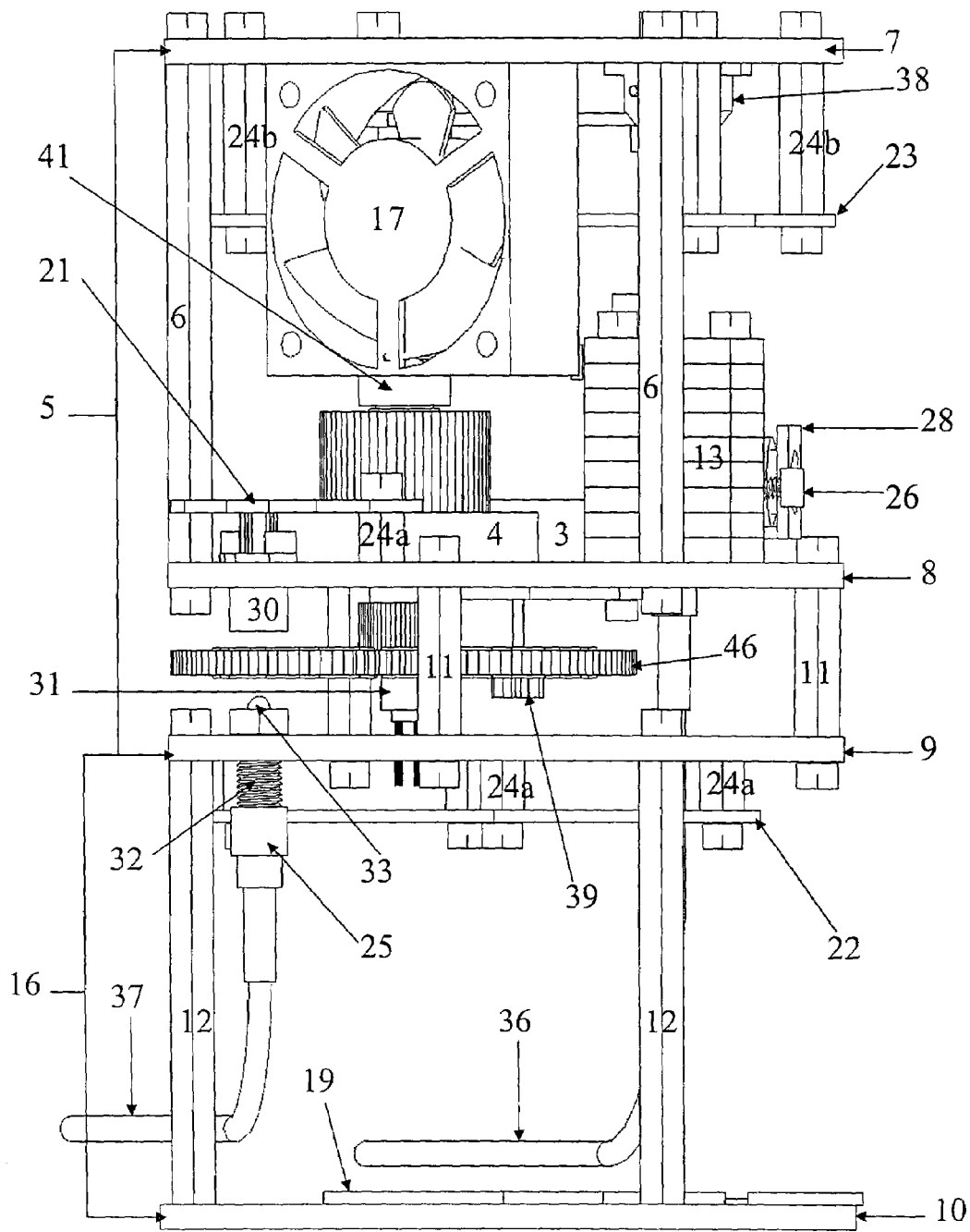
FIG. 5 is a component placement representation of the left view of the photometer of the present invention.
Figure 6:
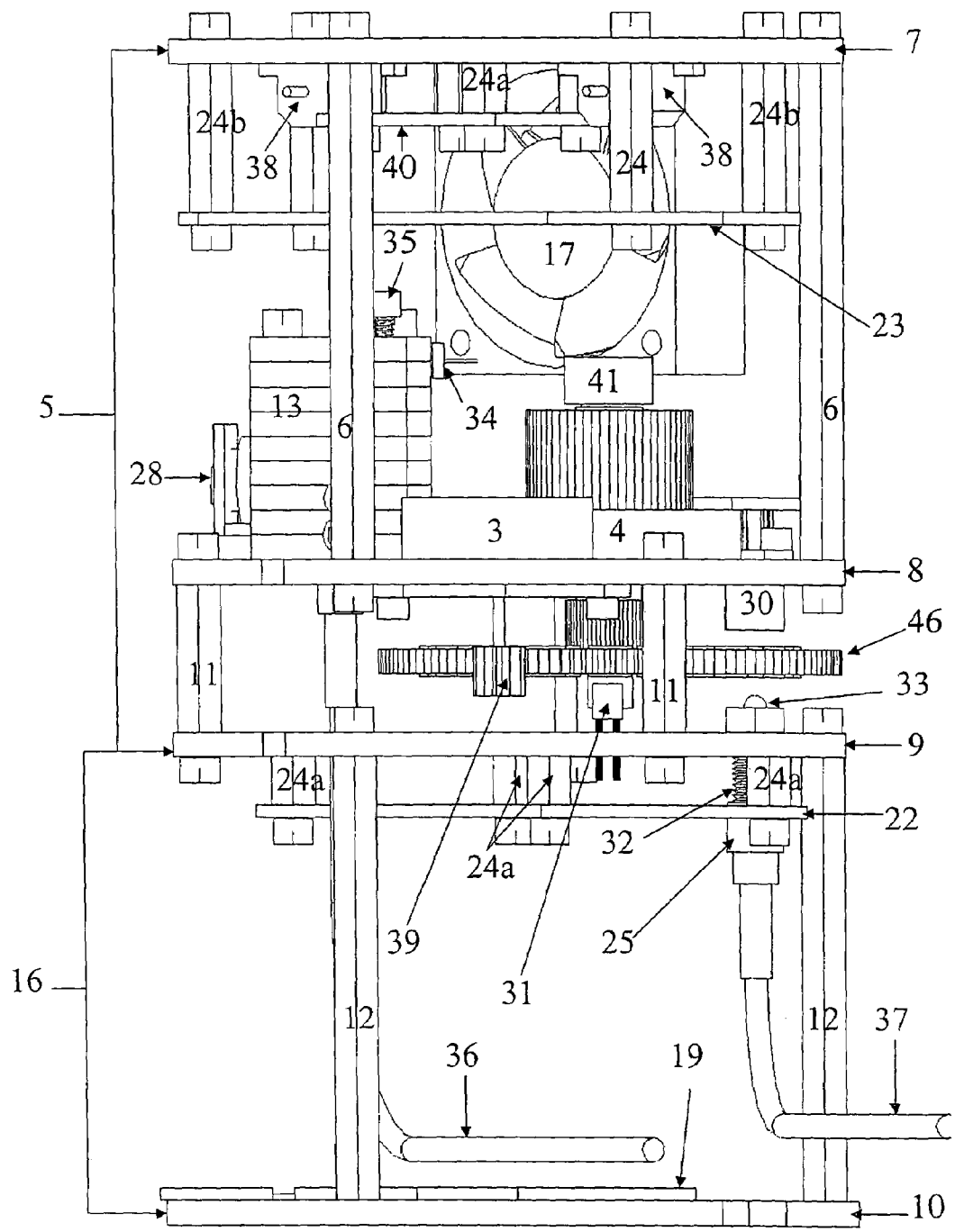
FIG. 6 is a component placement representation of the right view of the photometer of the present invention.
Figure 7:
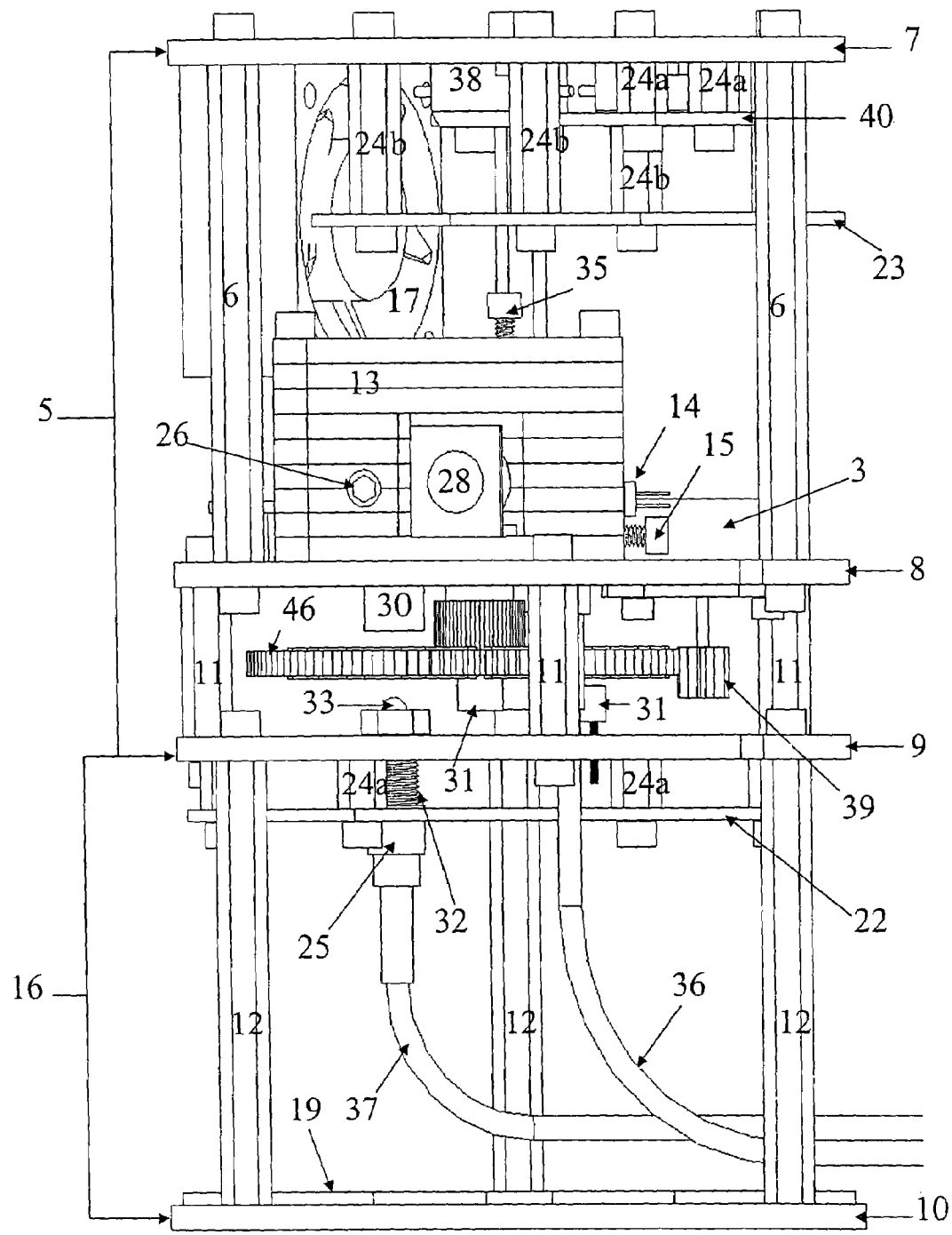
FIG. 7 is a component placement representation of the front view of the photometer of the present invention.
Figure 8:
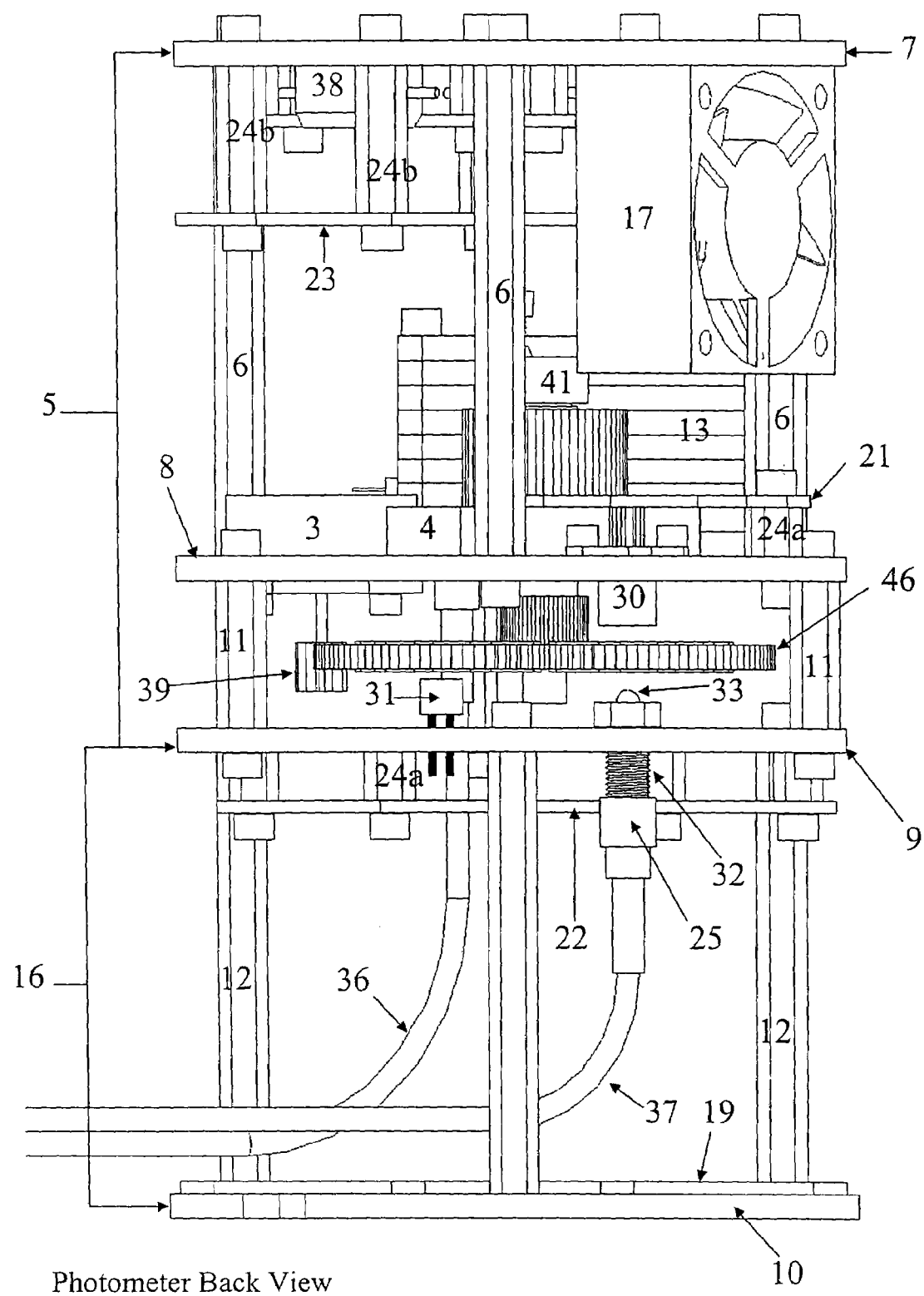
FIG. 8 is a component placement representation of the back view of the photometer of the present invention.

The present invention relates to a photometer suitable for in-line monitoring of a chemical production process which may be installed at the production site in close proximity to a stream of material to be monitored and to the method of monitoring a stream of material with such photometer.

Elements of the photometer of the present invention include: (a) a source of chopped radiation, preferably, an integrated optical source/chopper assembly such as that described in Applicants' co-pending application U.S. Ser. No. 10/983,404, filed on Nov. 8, 2004; (b) a remote sample cell or probe placed in a process stream or vessel in which the material to be analyzed is present; (c) optical fiber capable of relaying optical radiation output from the chopped radiation source (a) to the remote sample cell or probe (b); (d) a collimator; (e) optical fiber capable of relaying optical radiation from the remote sample cell or probe (b) to collimator (d); (f) a filter wheel assembly with multiple filters positioned so that the radiation beam output of collimator (d) intersects and is perpendicular to the filters on the wheel assembly; (g) means for detecting and controlling the position of the filter wheel; (h) a radiation detector positioned to receive collimated radiation from (d) after it has passed through the filter wheel assembly (f); (i) means for synchronous rectification of the output of radiation detector (h) with the chopped phase output signal of the chopped radiation source (a); (j) means for converting DC voltage output of rectifier (i) to a digital signal; (k) means for maintaining the collimated, chopped radiation source, the collimator, the filter wheel assembly, the radiation detector, the rectifier and the converter at a constant temperature; (l) a power supply; (m) a computer or some comparable means for controlling movable elements, for processing data and for communicating analytical results; (n) support for the chopped radiation source assembly, the filter wheel assembly, the radiation detector and the means for detecting and controlling position of the filter wheel that is rigid, and maintains position and optical alignment of those components without undue stress or strain on these components; (o) support for the power supply that will also act as a heat-sink and dissipate heat to the environment outside of the photometer housing; and (p) support for the rectifier, digital conversion means and temperature control component. An important feature of the photometer of the present invention is selection and arrangement of the photometer components in a manner such that the volume occupied by those components is small and that the critical components remain stationary during transport and use.

The photometer of the present invention will be described in greater detail with reference to FIGS. 1-9 which illustrate a preferred embodiment of the invention.

The photometer of the present invention 1 is made up of at least two different compartments. It is preferred that both compartments of photometer 1 be completely encased in a housing (not shown) which is a small as possible and which is explosion proof. A particularly preferred housing will measure less than 229 cubic inches (7.25×5.50×5.75 inches; 18.4×14.0×+14.6 cm (3761 cubic cm)). Such small, explosion-proof housings are commercially available. One such commercially available housing is the FM Approved Enclosure which is made of cast aluminum and produced by Adalet, a division of the Scott Fetzer Company.

The upper compartment 5 of photometer 1 is temperature controlled. The lower compartment 16 need not be temperature controlled and is preferably not temperature controlled.

In the illustrated photometer 1, compartments 5 and 16 are formed by circular metal plates 7, 8, 9 and 10 and support posts 6, 11 and 12. Plates 7, 8, 9 and 10 preferably have the same shape and circumference or perimeter. The shape of plates 7, 8, 9 and 10 is not, however, an essential feature of the present invention. Any shape would be useful. It is not necessary for these plates to have the same circumference or be made of the same material. It is particularly preferred that each of plates 7, 8, 9, and 10 be made of metal or some other material which is sufficiently rigid, strong and durable to support the photometer components and withstand the environment in which the photometer will be used. It is most preferred, however, that each of these plates be made of the same material and have the same circumference or perimeter for ease of assembly, compactness, and economic reasons. The size of these plates must be at least sufficient to accommodate the components to be placed in the compartment but there is not a maximum size requirement. It is particularly preferred, however, that the size of plates 7, 8, 9 and 10 be kept to the minimum size necessary for economic, handling and space reasons. It is also particularly preferred that the plates be metal, preferably, steel, aluminum, brass, or any metal or alloy that is strong and rigid such as aluminum alloy 6061. Support means 6, 11 and 12 must be made of a material which is capable of supporting the components of the photometer. The support means 6, 11 and 12 are shown as posts but they need not be in the form of posts. The support means are preferably made of metal, most preferably, steel, aluminum or an aluminum alloy or brass. If the support means are posts, those posts must be at least long enough to form a chamber capable of containing all of the required components for that compartment, posts designated by the same reference numeral must all be equal in length and at least three posts of equal length must be used for each compartment or chamber.

Upper compartment 5 is formed by plates 7, 8 and 9 and by support posts 6 and 11. Support posts 6 and 11 are preferably made of a metal, most preferably, steel, aluminum, brass, or any metal or alloy that is strong and rigid such as aluminum alloy 6061. Posts 6 must be at least long enough to form a compartment between plates 7 and 8 which will accommodate the components of the analyzer to be located between those plates. Posts 11 must be at least long enough to support the filter wheel 46 of filter wheel assembly 2 between plates 8 and 9. The total height of posts 6 and 11 must be high enough to accommodate the components of the analyzer which must be in the temperature controlled environment. Each of the posts 6 must be equal in length. Similarly, each of posts 11 must be equal in length. While posts 6 are used to support plates 7 and 8, it is not necessary that the support means for plates 7 and 8 be in the form of a post. Similarly, it is not necessary that the support means between plates 8 and 9 be in the form of posts. It would also be possible, for example, to support the plates with a "wall" formed by a cylinder made of a sturdy material, preferably metal, which has a circumference or perimeter equal to that of the plates being supported and height sufficient to accommodate the analyzer components which must be in the temperature controlled environment. However the use of a wall or walls to separate and support plates 7, 8, and 9 will restrict access to components placed within. Where support posts 6 are employed, the use of at least three posts will ensure that plates 7 and 8 are each supported at a minimum of three points which define a plane and do not stress and warp plates 7 and 8. Similarly, when posts are used as plate support means 11, at least three posts are generally employed to eliminate stress on plates 8 and 9. In like manner, plates 9 and 10 are preferably supported by at least three posts 12 to eliminate stress on plates 9 and 10.

In order to maximize optical throughput, ease alignment, and improve stability, the open path distance between optical components in the optical train is minimized.

The chopped radiation source included in the photometer of the present invention is composed of (1) a radiation source component, (2) a chopper component, and (3) an optical fiber connector component. It is preferred that each of these components be positioned in a housing in a manner such that the elements of each of these components will not move in an unintended manner during use. It is, however, also possible to mount each of these individual components to a plate or plates within temperature controlled chamber 5. When the radiation source component, chopper component and optical fiber component are not all included within the same housing, it is necessary to ensure that these components are properly aligned so that the radiation emitted from the radiation source will be chopped and will be relayed by the optical fiber.

Key elements of the radiation source component are (a) a radiation source 29, (b) means for directing (such as beam director 27) radiation emitted by the source 29 through a condensing element to concentrate the radiation to a focal point, and (c) a condensing element for concentrating the radiation to a focal point. The radiation source 29 may be any source of visible, ultraviolet and/or near infrared ("NIR") radiation known to those skilled in the art. It is preferred that the radiation emitted by radiation source 29 be collimated, however, any source of radiation which is not collimated when emitted may be made collimated by techniques known to those skilled in the art, such as passage through an aspheric lens. Examples of preferred radiation sources include tungsten filament lamps and light emitting diodes. Selection of an appropriate radiation source will, of course, be dependent upon the particular application for which the chopped optical source will be used.

It is desirable that the intensity of the radiation source be held at a constant level by, for example, a servo feedback loop controller and that a means for adjusting the intensity control set point be included. Intensity control and set point adjustment are not necessary when the radiation source is selected to meet a specific requirement or when that radiation source will be replaced before it nears the end of its useful life. However, it is generally advantageous to include means for setting the radiation intensity from source 29 with an adjustable "iris" such as a machine screw 35 that can be positioned to stop part of the radiation that reaches the radiation intensity feedback detector 34. The radiation intensity feedback detector 34 can be any optical radiation detector. Suitable feedback detectors include phototransistors and/or photodiodes. Such adjustment and control allows greater flexibility in selection of the radiation source and the ability to continue use of the radiation source after it has passed its peak performance. Suitable adjustable "irises" and detectors are known to those skilled in the art.

In the present invention, the radiation source component includes a beam director 27 which "folds" the collimated beam from source 29 to confine it in such a way that all of the required optical parts of the photometer of the present invention can be properly arranged in the restricted space within the temperature controlled compartment of the photometer. It is, of course, possible to place the optical components of the photometer of the present invention along one axis and thereby eliminate the need for beam director 27. Suitable beam directors include any of the known prisms and/or front surface mirrors.

To couple the source beam to the output optical fiber, a condensing optical element is included in the radiation source component. Suitable condensing elements include aspheric lenses, convex lenses, ball lenses and off-axis mirrors.

The chopping component of the chopped radiation source will generally include (a) a vibrating reed, tuning fork or any other known means for interrupting radiation flow at regular intervals, (b) a means for adjusting the duty cycle of the interruptions in radiation flow, and (c) a chopper phase detector 14. The chopper phase detector 14 should be positioned so that it will receive chopped radiation emanating from the optical fiber connector component. The chopper phase detector 14 is generally an optical radiation detector such as a phototransistor.

The optical fiber connector component holds the optical fiber positioned to receive chopped radiation, in the correct position, preferably, at the focal point of chopped radiation which has been passed through a condensing lens. In a preferred embodiment of the invention, the terminal portion of the optical fiber by which the chopped radiation is transmitted to the sample to be analyzed is encased by the connector. In a particularly preferred embodiment of the invention, there is an opening in the connector which leaves a minor portion of the optical fiber exposed. This opening may be positioned so that any radiation emitted through that opening can be detected by chopper phase detector 14.

In one of the preferred embodiments of the present invention, means for detecting the intensity of the radiation emitted by the source and means for adjusting the amount of radiation to be chopped are included in the radiation source component.

In another embodiment of the invention, a lock-in amplifier is synchronized with the output of an electrical pulse from chopper phase detector 14 which is in phase with the chopper which electrical pulse is derived from the radiation emitted at the opening of the optical fiber component housing.

A particularly preferred output optical path train is achieved with the integrated optical source/chopper assembly 13 described in detail in Applicants' co-pending application U.S. Ser. No. 10/983,404 filed Nov. 8, 2004 and incorporated herein by reference. In the chopped radiation source described in U.S. Ser. No. 10/983,404, for example, the open path distance is approximately 0.375 inches (0.95 cm) between the radiation source 29 and the end face of the output optical fiber 36. The return optical path train comprising the return optical fiber 37, collimating lens 33, filters 18, and radiation detector 30 has an open path distance of approximately 0.625 inches (1.6 cm).

In order to maintain alignment between optical components, the integrated optical source/chopper assembly 13, radiation detector 30, and filter wheel assembly 2 are all mounted on plate 8. Placement of these optical components on the same rigid plate and within close proximity to one another restricts movement that can affect alignment and/or stability. The end face of the return optical fiber 37 is fixed in place by SMA connector 25 at the focal point of collimating lens 33 mounted in housing 32 made from a modified SMA union that is mounted on plate 9. The distance between plates 8 and 9 is minimized to improve optical throughput, and stability of the return radiation beam between the return optical fiber 37 and the radiation detector 30 by minimizing the length of support posts 11.

Temperature control of chamber 5 may be achieved by enclosing that chamber in an insulating material or container (not shown) and circulating heated air with fan 17. Appropriate temperatures for chamber 5 will generally be at least 15° C. above ambient temperature, preferably, between 35 and 65° C., and most preferably from 45 to 55° C. The temperature in chamber 5 should be kept relatively constant. As used herein, a relatively constant temperature is a temperature which varies by no more than plus or minus 5° C. The outputs of resistance heating elements 38 are driven by a closed loop servo control circuit on printed circuit board ("PCB") 40 with input from an integrated circuit ("IC") temperature sensor also on PCB 40 and exposed to the heated air output of fan 17. Openings such as opening 20 are present on plate 8 to allow air circulation between the two sections of chamber 5 divided by plate 8.

The chopped radiation from assembly 13 is relayed to a remote insertion probe or flow through cell for process analysis of the material in the optical path of the probe or flow through cell via the output optical fiber 36. Fiber 36 is inserted into assembly 13 via a modified SMA connector and held in place by an appropriate fastener 15 (e.g., a screw). The remote probe or flow through cell is not shown, as it is application dependent and is not a component of the photometer of the present invention. Choice of a suitable insertion probe or flow through cell will be apparent to those skilled in the art. The radiation is passed through the material being monitored and relayed via return optical fiber 37, connected by SMA connector 25 to modified SMA union 32. SMA union 32 also houses collimating ball lens 33. The output radiation beam from the end face of return optical fiber 37 is collimated, e.g., by ball lens 33 and is passed through the filters 18 on filter wheel 46 and then to detector 30. The output of detector 30 is conditioned by the preamplifier on printed circuit board (PCB) 21 and relayed via cabling to the lock-in amplifier on PCB 23. In the illustrated embodiment of the invention, PCB 23 is held in position by posts 24 which are affixed to plate 7. The chopped radiation source 13 which is preferably an integrated optical source/chopper assembly of the type disclosed in Applicants' co-pending application U.S. Ser. No. 10/983,404 detects and outputs a chopper phase pulse via phototransistor 14. The duty cycle of the chopped radiation is adjusted by any suitable means such as by turning an adjusting means 26 shown in the Figures as a screw. The chopper phase pulse is relayed from phototransistor 14 to a lock-in amplifier on PCB 23 via cabling and is used to synchronize the detection of the conditioned signal from detector 30. The DC signal from the output of the lock-in amplifier is filtered and converted to a digital signal via an analog to digital converter on PCB 23. The integrated optical source/chopper assembly 13, detector 30, preamplifier on PCB 21, and lock-in amplifier and analog to digital converter on PCB 23 are all in temperature controlled chamber 5 to stabilize the temperature dependent electronic circuits.

The digital output of the analog to digital converter on PCB 23 is relayed via cabling to the microprocessor on PCB 22 located in the lower compartment or chamber 16. Compartment 16 is formed from plates 9 and 10 and posts 12. The microprocessor on PCB 22 dose not have to be in a temperature controlled chamber because digital signals are inherently temperature independent. The microprocessor also controls the positioning and synchronizing of the filter wheel 46 via stepper motor 3 and optical-interrupter 31. Optical-interrupter 31 detects the edge of a marker or flag on a highly reflective surface of the filter wheel 46 to determine the zero position of the filter wheel 46. The center position of each filter 18 on filter wheel 46 is measured in terms of the number of pulses of the stepper motor 3 required to reach that center position from the zero position. This measurement for each filter 18 is stored in memory in the microprocessor on PCB 22. To position the filter wheel to a given filter, the microprocessor outputs a direction pulse and a given number of step pulses to a stepper motor driver integrated circuit (IC) also located on PCB 22. The stepper motor driver IC synchronizes the coil sequencing and provides current gain necessary to drive the stepper motor 3. The output of the stepper motor 3 is relayed via gear 39 to the filter wheel 46. The microprocessor on PCB 22 also outputs the drive pulse to a chopper solenoid 28 located on the integrated radiation source/chopper assembly 13. Where a chopper assembly that includes a vibrating reed (such as that disclosed in Applicants' co-pending application U.S. Ser. No. 10/983,404) is used as the chopped radiation source 13, the resonant frequency of the vibrating reed chopper may be stored in memory and used to synchronize the chopper drive. The microprocessor also has an internal multi-channel 10-bit analog to digital converter that accepts inputs from integrated circuit (IC) temperature sensors, and voltage test points to monitor operational parameters of the photometer.

Additionally, the microprocessor on PCB 22 communicates with an external device such as a computer (not shown) via cabling to receive operational commands, and relay photometer status and analytical results. Photometer 1 in this embodiment receives operational instructions from the external device. In a typical sequence of events, the filter wheel 46 is brought to the edge of the zero position (which is generally "marked" with, for example, a flag (not shown)) on filter wheel 46; filter wheel 46 is moved in a clockwise direction to position a given filter 18 between detector 30 and collimating lens 33; a selected number of time averaged readings of the detector 30 are collected; the collected readings are relayed back to the external device; filter wheel 46 is then moved in a clockwise direction to position the next desired filter between detector 30 and collimating lens 33; detector reading(s) are collected and relayed to the external device(s); these steps are repeated until all desired filters are scanned. The external device can be any computer capable of performing basic logical sequencing and computational analysis and of providing analytical results, preferably, in the form of text, graphical representation, or signal output such as a voltage or current. In a preferred embodiment of this invention, the photometer responds to a few simple commands given by a computer which controls the operation of the photometer and performs all computations. Such external control and computation allows upgrading of photometer performance without opening or servicing the photometer 1 after installation. Use of such an external control and computational device is not, however, an essential feature of the present invention.

In another embodiment of the present invention, the microprocessor on PCB 22 may be programmed to sequence filter wheel 46; collect readings from detector 30; and calculate and output analytical results either digitally or as a voltage, frequency or current signal.

Located in chamber 16 on plate 10 is printed circuit board (PCB) 19 on which are located switching or digital power supplies. The switching power supplies are located at the base of photometer 1 on PCB 19 so that any heat emanating from them will be heat sunk via plate 10 to the housing and the outside environment. 24 volt, 1.5 amp power is provided to photometer 1 by an external power source (not shown) via cabling and is converted to +12 volts, +5 volts, and −12 volts to operate the analog and digital circuitry on PCB's 19, 21, 22, and 23. The externally supplied power is also relayed via cabling directly to the heater control circuits on PCB 40 located in chamber 5, on plate 7, that drive resistance heaters 38 (shown in FIG. 5).

Not shown in FIGS. 1-9 is the cabling to the external power supply and to the external computer(s). The cabling, although it may be necessary to operate some embodiments of the photometer of the present invention, is not an essential feature of the photometer itself. Suitable cabling and interconnect methods will be known to those skilled in the art.

In the illustrated embodiment of the present invention, slots 48 are cut in plates 8 and 9 to accommodate cabling between chambers 5 and 16.

Also not shown in detail in FIGS. 1-9 are the specific circuits for detector 30 preamplifier, lock-in amplifier, analog to digital converter, microprocessor, stepper motor driver, optical interrupter, temperature control, and switching power supplies. Integrated circuits which may be used for each of these components of the photometer of the present invention are commercially available. Selection of appropriate circuits is within the skill of those in the art. Examples of suitable, commercially available integrated circuits are given in the example below.

Figure 9:
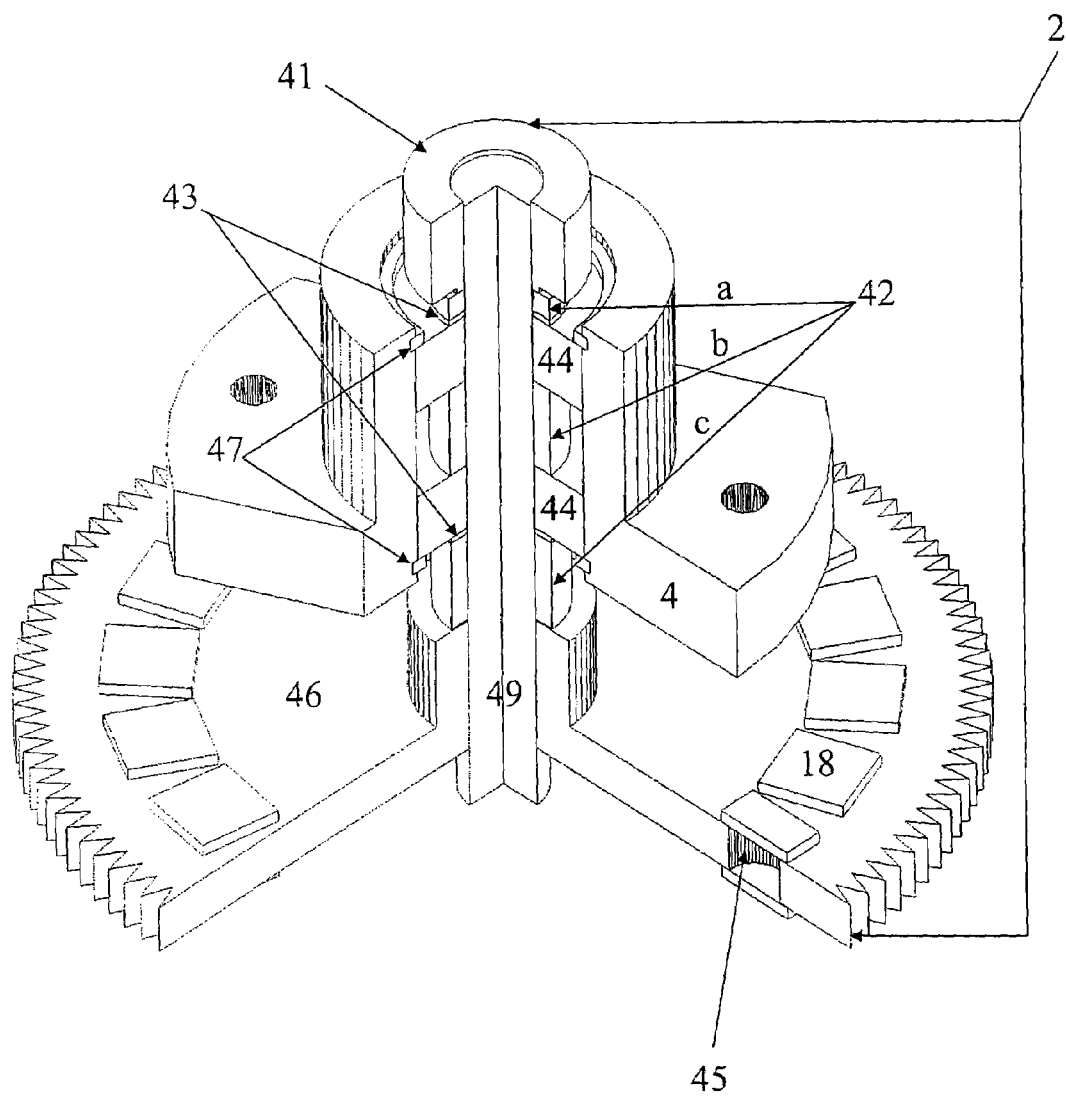
FIG. 9 is a cut away vies of a component placement representation of a filter wheel assembly.

Filter wheel assembly 2 is shown in greater detail in FIG. 9. As can be seen in FIG. 9, filter wheel assembly 2 includes one or more filters 18 which are capable of passing radiation at selected wavelengths. The number of filters 18 present on filter wheel 46 is preferably from 3 to 30, more preferably from 5 to 18, most preferably, from 7 to 18. The particular filters are selected on the basis of the materials to be monitored. Specifically, filters having band-pass wavelengths of radiation which would be absorbed by the material(s) being monitored are selected. The filters are evenly spaced on the wheel. One band-pass filter at wavelengths that are not absorbed by the material being monitored is also included on the wheel to provide a reference wavelength. Any of the commercially available filters which pass the desired wavelengths may be used on filter wheel 46.

Filter wheel assembly 2 includes: bearing mount 4, filters 18, shaft 49, shaft collar 41, spacers 42, springs 43 (e.g., wave springs or coil springs), bearings 44, filter openings 45, filter wheel 46, and snap rings 47. Filters 18 may be mounted on the surface of filter wheel 46 as shown in FIG. 9 or they may be mounted in the filter openings 45. Near infrared (NIR) band-pass filters are generally made from two thin sections that are sandwiched together in a manner such that one section is a narrow band-pass filter and the other section is a blocking filter. In the illustrated embodiment, the two sections are scribed and broken into smaller pieces that will fully cover opening 45. One section is mounted on one side of opening 45 and the other section is mounted on the opposite side as shown in FIG. 9. In another embodiment, when the photometer is used in the visible region of the spectrum, the filters may be thicker and can be mounted in the opening 45.

Having thus described our invention, the following Example is given as being illustrative thereof.

EXAMPLE

A device corresponding to that shown in FIGS. 1-9 utilizing the chopped radiation assembly disclosed in Applicants' co-pending application U.S. Ser. No. 10/983,404 filed Nov. 8, 2004 was constructed of the materials listed below and housed in an explosion proof ADALET# XIHLDCX Class I Division 1 Groups B,C,D Enclosure.

Filter wheel Assembly 2 was constructed of the following materials:

Bearing housing 4 A housing designed to mount two 0.625 inches (1.588 cm) outside diameter by 0.196 inches (0.498 cm) high bearings spaced 0.163 inches (0.414 cm) apart which is made of aluminum.

Shaft 31 A shaft measuring 0.25 inches (0.635 cm) in diameter and 1.75 inches (4.445 cm) long made of 303 stainless steel.

Set Screw Collar 41 A ring having an inner diameter of 0.25 inches (0.635 cm), an outer diameter of 0.5 inches (1.27 cm), a height of 0.25 inches (0.635 cm) with $6/_{32}$-thread steel set screw made of aluminum.

Spacer(s) 42*a* A 0.063 inches long tube with an inner bore of 0.25 inches (0.635 cm) and an outside diameter of 0.375 inches (0.953 cm) made of 303 stainless steel.

Spacer(s) 42*b* A 0.014 inches (0.036 cm) long tube with an inner bore of 0.25 inches (0.635 cm) and an outside diameter of 0.375 inches (0.953 cm) made of 303 stainless steel.

Spacer(s) 42*c* A 0.375 inches (0.953 cm) long tube with an inner bore of 0.25 inches (0.635 cm) and an outside diameter of 0.375 inches (0.953 cm) made of 303 stainless steel.

Washer Spring(s) 43 Wave washer springs made of 303 stainless steel and measuring 0.006 inches (0.015 cm) thick with an inside diameter of 0.265 inches (0.673 cm) and an outside diameter of 0.367 inches (0.932 cm).

Ball Bearings 44 Ball bearings measuring having a 0.25 inches (0.635 cm) bore with an outside diameter of 0.625 inches (1.588 cm) and a height of 0.196 inches (0.498 cm) made of 440C stainless steel.

Opening 45 Drilled or laser cut measuring 0.188 inches (0.476 cm) in diameter.

Filter Wheel 46 A 48-pitch spur gear with 120 teeth, a bore of 0.25 inches (0.635 cm) and outside diameter of 2.542 inches (6.457 cm) made of 2024 aluminum having 18 openings for placement of filters thereon.

Snap Rings 47 Snap rings made of carbon spring steel for a housing diameter of 0.625 inches (1.588 cm) and thickness of 0.035 inches (0.089 cm).

Slots 48 laser cut clots in plates 8 and 9 for interconnect cabling passage.

Stepper motor 3 A unipolar stepper motor having 48 steps/revolution measuring 26 mm in diameter having a height of 12.7 mm, with a 2 mm shaft and a 9.2 mNm/1.3 ozin holding torque.

Support posts 6 Posts made of aluminum measuring 2.5 inches (6.35 cm) long by 0.25 inches (0.635 cm) in diameter.

Plates 7, 8, and 9 Plates having a 3.75 inch (9.525 cm) diameter which are 0.125 inch (0.318 cm) thick and are made of 6061 grade aluminum.

Plate 10 A plate having a 4.00 inch (10.16 cm) diameter which is 0.125 inch (0.138 cm) thick and is made of 6061 grade aluminum.

Support posts 11 Posts made of aluminum measuring 0.75 inches (1.905 cm) long by 0.25 inches (0.635 cm) diameter.

Support posts 12 Posts made of aluminum measuring 2.00 inches (5.08 cm) long by 0.25 inches (0.635 cm) in diameter.

Chopped radiation assembly 13: Described in detail in Applicants' co-pending application U.S. Ser. No. 10/983,404 filed Nov. 8, 2004, is composed of the following:

Phase Detector 14 A phototransistor having a peak wavelength sensitivity of 880 nm and a radiation acceptance angle of 8°.

Locking Screw 15 A 4/40 thread machine screw measuring 0.375 inches (0.953 cm) long.

Duty cycle adjuster 26 A 4/40 thread machine screw measuring 0.5 inches (1.27 cm) long.

Beam steering mirror 27 Part of assembly 13 is a front surface mirrormirror measuring 0.25 inches (0.635 cm) by 0.25 inches (0.635 cm) square and 0.063 inches (0.159 cm) thick.

Solenoid 28 A solenoid coil with a DC resistance of 27 ohms measuring 0.50 inches (1.27 cm) in diameter and 0.625 inches (1.588 cm) long.

Radiation Source 29 A tungsten filament lamp which emits radiation at wavelengths of from 400 nm to 2500 nm.

Intensity Detector 34 wavelength sensitivity of 880 nm and a radiation acceptance angle of 8°.

Adjustable Iris 35 A 4/40 thread machine screw measuring 0.375 inches (0.953 cm) long.

Output Fiber 36 Part of assembly 13 is a 500 um diameter low OH optical fiber.

Circulating fan 17 A brushless 8500-RPM fan measuring 40 mm by 40 mm by 20 mm.

Filters 18 Spectrogon NIR filters (Wavelength selected on the basis of the sample material to be evaluated).

Power supply board 19 Supports the following circuits: +12 Volt, 1.0 Amp DC to DC converter which is manufactured by Texas Instruments (PT5102N); +5 Volt, 1.5 Amp DC to DC converter which is manufactured by Texas Instruments (78ST105HC); −12 Volt, 0.5 Amp DC to DC converter which is manufactured by Texas Instruments (PT5024N); and N channel MOSFET power transistor used to drive the two stage thermoelectric cooler of Detector 30.

Plate Hole 20 Opening measuring 0.375 inches (0.953 cm) which is cut in air circulation in Chamber 5

Preamplifier circuit board 21 Supports high impedance input, low noise operational amplifier integrated circuit manufactured by Burr-Brown (OPAL 111 AM)

Microprocessor board 22 Supports the following circuits: 40 pin CMOS Microprocessor having 8 K of Flash program memory, 386 bytes of data RAM, and a 5 channel 10 bit A/D converter manufactured by Microchip Inc. (PIC 16F877); Stepper Motor Drive integrated circuit capable of providing unipolar coil sequencing for the stepper motor drive which is manufactured by Allegro (UCN5804B); Temperature Sensor integrated circuit capable of generating a 10+mv/° K output signal which is manufactured by National Semiconductor (LM335)

Analog circuit board 23 Supports the following circuits:
Lock-in Amplifier integrated circuit capable of balanced demodulation, a bandwidth of 2 MHz, programmable gain, and 45 V/us slew rate which is commercially available from Analog Devices (AD630); 24 Bit Analog to Digital Converter integrated circuit which is capable of 6 conversions per second, 4 ppm scale error, 0.3 ppm noise, and 0.5 ppm offset which is manufactured by Linear Technology (LTC2400); Operational Amplifier integrated circuit capable of ultra low noise amplification of 4.5 nV/√Hz maximum at 1 KHz and 100 μV offset maximum which is manufactured by Burr-Brown (OPA27); Temperature Sensor integrated circuit which is capable of generating a +10 mv/° K output signal which is manufactured by National Semiconductor (LM335); Pulse Phase Shifter Circuit which is commercially available from NEC (2N5457 JFET); and A Precision +5 Volt Reference capable of 0.05% accuracy and 5 ppm/° C. drift which is manufactured by Linear Technology (LTC 1236).

Support Posts 24*a* Posts made of aluminum measuring 0.25 inches (0.635 cm) long and 0.25 inches (0.635 cm) in diameter.

Support Posts 24*b* Posts made of aluminum measuring 0.75 inches (1.905 cm) long and 0.25 inches (0.635 cm) in diameter.

SMA Fiber Optic Connector 25 SMA fiber optic connector used to terminate a 500 μm diameter glass fiber.

Detector 30 1 mm square, two stage thermoelectric cooled PbS detector manufactured by NEP (D2-1-37).

Filter Wheel Zero Flag Detector 31 Reflective optical interrupter made up of a light emitting diode and a phototransistor placed side by side.

SMA Bulkhead Union 32 Standard SMA bulkhead adapter drilled to accept a 0.25 inch (0.635 cm) ball lens manufactured by Amphenol.

Collimating Lens 33 A sapphire ball lens measuring 0.25 inches (0.635 cm) in diameter.

Return Optical Fiber 37 500 um Low OH Glass Fiber terminated with SMA Connector 25.

Heater Resistor 38 25 ohm, 5 watt resistor.

Spur Gear 39 A 48-pitch spur gear with 14 teeth, a bore of 2 mm, 0.635 mm long with an outside diameter of 0.846 cm made of brass.

Heater Control PCB 40 Supports the following circuits: A 3 terminal voltage regulator integrated circuit capable of 3 amp output manufactured by Fairchild (LM350); Temperature Sensor integrated circuit capable of generating a +10 mv/° K output signal which is manufactured by National Semiconductor; and Voltage Reference integrated circuit manufactured by National Semiconductor (LM329).

An apparatus corresponding to that illustrated in FIGS. 1-9 was made with the above-described components. This device was then used to determine the distillation residue content in an opaque, dark-colored mixture containing an isocyanate and tar-like materials (residue) during the isocyanate production process. This information is critical to controlling and optimizing the distillation process. The apparatus of the present invention made chemometric calibration possible because it has the capability of evaluating a much larger number of wavelengths which can be distributed over the bands of interest. The apparatus of the present invention has been proven at two different residue monitoring points in the isocyanate production process.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process photometer comprising
   a) an insulated compartment maintained at a relatively constant, elevated temperature which houses:
      (1) a source of chopped radiation directed to a focal point,
      (2) a means for detecting the chopped radiation's phase and generating a phase pulse,
      (3) an output optical fiber to convey the chopped radiation from the focal point to a remote sample, the fiber having one end supported by (4) a connector which holds the supported end of the optical fiber stationary at the radiation focal point,
(5) a rotatable filter wheel having at least one filter for a radiation wavelength band modulated by each material being monitored,
(6) means for rotating the filter wheel a regular, pre-determined distance at regular, pre-determined time intervals,
(7) a return optical fiber to relay radiation modified by a material being analyzed from a remote sample cell to a filter on the filter wheel,
(8) a radiation detector for radiation which has passed through a filter on the filter wheel,
(9) a preamplifier for low noise amplification of output from the radiation detector,
(10) a lock-in amplifier for synchronized detection of output from the preamplifier with chopped radiation phase pulse,
(11) a means of converting the analog output from the lock-in amplifier to a digital signal,
(12) means for maintaining a relatively constant temperature in compartment a), and
(13) means for securing the components housed in compartment a) in the insulated compartment in a manner such that they are held in proper position, and b) a non-insulated compartment which houses a power supply, and c) a means for controlling movement of the filter wheel which may be located in the insulated compartment, in the non-insulated compartment or external to both compartments a) and b).

2. The photometer of claim 1 in which the insulated compartment is maintained at a temperature of from 15° above ambient temperature to about 65° C.

3. The photometer of claim 1 in which compartments a) and b) are housed in an explosion-proof enclosure.

4. The photometer of claim 1 in which the source of radiation is a tungsten filament bulb.

5. The photometer of claim 1 in which the means for condensing the radiation to a focal point is a sapphire ball lens.

6. The photometer of claim 1 in which the filter wheel has from 3 to 32 filters.

7. The photometer of claim 1 in which the filter wheel has from 5 to 18 filters.

8. The photometer of claim 1 in which the filter wheel has from 7 to 8 filters.

9. The photometer of claim 1 in which the filter wheel is moved by a stepper motor which is connected to the filter wheel in a manner which allows that motor to move the filter wheel a pre-set distance after a given period of time.

10. The photometer of claim 9 in which each filter on the filter wheel is positioned an equal distance from each adjacent filter.

11. The photometer of claim 10 in which the pre-set distance the filter wheel is moved is the distance from the midpoint of one filter on the filter wheel to the midpoint of the next filter on the filter wheel.

12. The photometer of claim 1 in which a computer is used to control the movement of the filter wheel.

13. The photometer of claim 1 which further comprises a computer for controlling the movement of the filter wheel, mathematical processing of data collected and communication of results of data processing.

14. The photometer of claim 1 in which a vibrating reed having a resonance frequency between 30 and 1000 Hz is the radiation chopper.

15. The photometer of claim 1 in which the source of near infrared radiation has an incandescent filament.

16. The photometer of claim 1 in which the source of radiation is a light emitting diode.

17. A photometer comprising
a) an insulated compartment maintained at a constant, elevated temperature enclosing components comprising:
(1) a source of chopped radiation,
(2) means for detecting intensity of radiation emitted from the chopped radiation source,
(3) means for adjusting intensity of the radiation emitted from the chopped radiation source,
(4) means for controlling the intensity from the chopped radiation source at the adjusted intensity level
(5) means for directing the radiation emitted by the chopped radiation source to
(6) a transmitter for the radiation emitted by the chopped radiation source to a sample,
(7) a filter wheel having at least one filter for a radiation wavelength emitted by each material being monitored,
(8) means for moving the filter wheel a regular, pre-determined distance at regular, pre-determined time intervals,
(9) a lens through which the chopped radiation emitted by chopped radiation source has hat has been passed through the sample is directed through a filter on the filter wheel,
(10) a radiation detector to receive the radiation passed through the lens,
(11) means for maintaining a relatively constant temperature in compartment a), and
(12) support means for components in compartment a), and b) a non-insulated compartment enclosing a component comprising a power supply, c) a means for controlling movement of the filter wheel which may be located in the insulated compartment, the non-insulated compartment or be external to compartments a) and b), and d) a receiver for radiation emitted by the chopped radiation source that has been passed through a sample in which each of the components is fixed in an arrangement which ensures proper alignment of the components during use.

18. The photometer of claim 17 in which intensity of near infrared radiation detected is used as input for a closed loop control.

19. The photometer of claim 17 in which a radiation chopper is placed between the radiation directing means and the transmitter.

20. The photometer of claim 19 in which the radiation chopper comprises a vibrating reed having a resonance frequency between 30 and 1000 Hz.

21. The photometer of claim 19 in which the radiation chopper is a piezoelectric chopper.

22. The photometer of claim 17 in which the transmitter is an optical fiber having a portion of its surface exposed to an opening in a connector so that coupled radiation propagating through the fiber radiates out of the fiber.

23. The photometer of claim 22 in which the minor amount of radiation radiating out of the optical fiber is used to synchronize a lock-in amplifier.

24. The photometer of claim 17 which further comprises a means for condensing radiation from the directing means before that radiation is transmitted by the transmitter.

25. The photometer of claim 24 in which the radiation condensing means is a sapphire ball lens.

* * * * *